(12) United States Patent
Bhullar et al.

(10) Patent No.: US 7,476,827 B1
(45) Date of Patent: Jan. 13, 2009

(54) METHOD OF MAKING A BIOSENSOR

(75) Inventors: Raghbir S. Bhullar, Indiananpolis, IN (US); Henning Groll, Indianapolis, IN (US); John T. Austera, Indianapolis, IN (US); Douglas P. Walling, Indianapolis, IN (US); Timothy L. Ranney, Lebanon, IN (US); James L. Pauley, Jr., Fishers, IN (US)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 866 days.

(21) Appl. No.: 10/976,740

(22) Filed: Oct. 29, 2004

Related U.S. Application Data

(62) Division of application No. 09/942,515, filed on Aug. 29, 2001, now Pat. No. 6,814,844.

(51) Int. Cl.
*B23K 26/38* (2006.01)
(52) U.S. Cl. .................................. 219/121.69
(58) Field of Classification Search ............ 219/121.69; 427/555, 556
See application file for complete search history.

(56) References Cited

U.S. PATENT DOCUMENTS

| | | |
|---|---|---|
| 4,081,653 A | 3/1978 | Koo et al. |
| 4,131,484 A | 12/1978 | Caruso et al. |
| 4,414,059 A | 11/1983 | Blum et al. |
| 4,476,149 A | 10/1984 | Poppe et al. |
| 4,592,893 A | 6/1986 | Poppe et al. |
| 4,671,661 A | 6/1987 | Ott |
| 4,707,722 A * | 11/1987 | Folk et al. ................... 257/741 |
| 4,865,873 A | 9/1989 | Cole et al. |
| 4,874,500 A | 10/1989 | Madou et al. |
| 4,897,173 A | 1/1990 | Nankai et al. |
| 4,963,814 A | 10/1990 | Parks et al. |
| 4,999,582 A | 3/1991 | Parks et al. |
| 4,999,632 A | 3/1991 | Parks |
| 5,018,164 A | 5/1991 | Brewer et al. |
| 5,089,103 A | 2/1992 | Swedberg |
| 5,104,480 A | 4/1992 | Wojnarowski et al. |
| 5,120,420 A | 6/1992 | Nankai et al. |

(Continued)

FOREIGN PATENT DOCUMENTS

EP  0 875 754  11/1998

(Continued)

OTHER PUBLICATIONS

LPKF MicrolineLaser II, LPKF Laser & Electronics AG; LPKF; Art.-Nr. 107645-2 (Jan. 2000) (2pp.).

(Continued)

*Primary Examiner*—Geoffrey S Evans
(74) *Attorney, Agent, or Firm*—Justin L. Sage; Roche Diagnostics Operations, Inc.

(57) ABSTRACT

The present invention relates to a method of forming a biosensor. The method includes providing a substrate coated with a electrically conductive material, ablating the electrically conductive material to form electrodes and a code pattern, wherein there is sufficient contrast between the conductive coating and the substrate such that the code pattern is discernible, and applying a reagent to at least one of the electrodes.

4 Claims, 4 Drawing Sheets

U.S. PATENT DOCUMENTS

| | | | |
|---|---|---|---|
| 5,243,516 | A | 9/1993 | White |
| 5,264,103 | A | 11/1993 | Yoshioka et al. |
| 5,266,179 | A | 11/1993 | Nankai et al. |
| 5,288,636 | A | 2/1994 | Pollmann et al. |
| 5,334,279 | A | 8/1994 | Gregoire |
| 5,336,388 | A | 8/1994 | Leader et al. |
| 5,352,351 | A | 10/1994 | White et al. |
| 5,366,609 | A | 11/1994 | White et al. |
| 5,382,346 | A | 1/1995 | Uenoyama et al. |
| 5,390,412 | A | 2/1995 | Gregoire |
| 5,391,250 | A | 2/1995 | Cheney, II et al. |
| 5,395,504 | A | 3/1995 | Saurer et al. |
| 5,405,511 | A | 4/1995 | White et al. |
| 5,413,690 | A | 5/1995 | Kost et al. |
| 5,414,224 | A | 5/1995 | Adasko et al. |
| 5,426,850 | A | 6/1995 | Fukutomi et al. |
| 5,437,999 | A | 8/1995 | Diebold et al. |
| 5,438,271 | A | 8/1995 | White et al. |
| 5,451,722 | A | 9/1995 | Gregoire |
| 5,465,480 | A | 11/1995 | Karl et al. |
| 5,496,453 | A | 3/1996 | Uenoyama et al. |
| 5,508,171 | A | 4/1996 | Walling et al. |
| 5,509,410 | A | 4/1996 | Hill et al. |
| 5,512,489 | A | 4/1996 | Girault et al. |
| 5,567,302 | A | 10/1996 | Song et al. |
| 5,575,930 | A | 11/1996 | Tietje-Girault et al. |
| 5,576,073 | A | 11/1996 | Kickelhain |
| 5,589,326 | A | 12/1996 | Deng et al. |
| 5,593,739 | A | 1/1997 | Kickelhain |
| 5,628,890 | A | 5/1997 | Carter et al. |
| 5,635,054 | A | 6/1997 | Girault et al. |
| 5,637,850 | A * | 6/1997 | Honda .................. 235/454 |
| 5,682,884 | A | 11/1997 | Hill et al. |
| 5,708,247 | A | 1/1998 | McAleer et al. |
| 5,739,039 | A | 4/1998 | Girault et al. |
| 5,755,953 | A | 5/1998 | Henning et al. |
| 5,758,398 | A | 6/1998 | Rijnbeek et al. |
| 5,759,364 | A | 6/1998 | Charlton et al. |
| 5,762,770 | A | 6/1998 | Pritchard et al. |
| 5,773,319 | A | 6/1998 | Chu et al. |
| 5,798,031 | A | 8/1998 | Charlton et al. |
| 5,945,341 | A | 8/1999 | Howard et al. |
| 5,948,289 | A | 9/1999 | Noda et al. |
| 5,955,179 | A | 9/1999 | Kickelhain et al. |
| 5,956,572 | A | 9/1999 | Kidoguchi et al. |
| 5,965,001 | A | 10/1999 | Chow et al. |
| 5,989,917 | A | 11/1999 | McAleer et al. |
| 5,997,817 | A | 12/1999 | Crismore et al. |
| 6,004,441 | A | 12/1999 | Fujiwara et al. |
| 6,036,092 | A | 3/2000 | Lappe |
| 6,103,033 | A | 8/2000 | Say et al. |
| 6,129,823 | A | 10/2000 | Hughes et al. |
| 6,134,461 | A | 10/2000 | Say et al. |
| 6,165,594 | A | 12/2000 | Moh et al. |
| 6,175,752 | B1 | 1/2001 | Say et al. |
| 6,203,952 | B1 | 3/2001 | O'Brien et al. |
| 6,258,229 | B1 | 7/2001 | Winarta et al. |
| 6,287,451 | B1 | 9/2001 | Winarta et al. |
| 6,295,506 | B1 | 9/2001 | Heinonen et al. |
| 6,299,757 | B1 | 10/2001 | Feldman et al. |
| 6,309,526 | B1 | 10/2001 | Fujiwara et al. |
| 6,338,790 | B1 | 1/2002 | Feldman et al. |
| 6,394,952 | B1 | 5/2002 | Anderson et al. |
| 6,399,258 | B2 | 6/2002 | O'Brien et al. |
| 6,436,256 | B1 | 8/2002 | Williams et al. |
| 6,540,890 | B1 | 4/2003 | Bhullar et al. |
| 6,599,406 | B1 | 7/2003 | Kawanaka et al. |
| 6,617,541 | B1 | 9/2003 | Wadman et al. |
| 6,638,772 | B1 * | 10/2003 | Douglas et al. .......... 436/518 |
| 6,645,359 | B1 | 11/2003 | Bhullar et al. |
| 6,662,439 | B1 | 12/2003 | Bhullar |
| 6,696,008 | B2 | 2/2004 | Brandinger |
| 6,875,327 | B1 | 4/2005 | Miyazaki et al. |
| 2003/0088166 | A1 | 5/2003 | Say et al. |
| 2003/0100030 | A1 | 5/2003 | Nadaoka et al. |
| 2003/0175946 | A1 | 9/2003 | Tokunaga et al. |
| 2004/0005721 | A1 | 1/2004 | Tanike et al. |
| 2004/0026254 | A1 | 2/2004 | Hupe et al. |

FOREIGN PATENT DOCUMENTS

| | | | |
|---|---|---|---|
| GB | 2 311 614 | A | 10/1997 |
| JP | 56100451 | | 8/1981 |
| JP | 2-247087 | A * | 10/1990 |
| JP | 5-315703 | | 11/1993 |
| JP | 7-60464 | A * | 3/1995 |
| JP | 7-66499 | | 3/1995 |
| JP | 7-290751 | | 11/1995 |
| JP | 9-260697 | | 10/1997 |
| JP | 10-52780 | | 2/1998 |
| JP | 10-241992 | | 9/1998 |
| JP | 10-275959 | | 10/1998 |
| JP | 10-303444 | | 11/1998 |
| JP | 11297890 | | 10/1999 |
| JP | 2000-019147 | A | 1/2000 |
| JP | 2000-121594 | | 4/2000 |
| JP | 2001-87874 | A * | 4/2001 |
| JP | 2000-212760 | A * | 8/2002 |
| WO | WO 91/02391 | | 2/1991 |
| WO | WO 98/35225 | | 8/1998 |
| WO | WO 98/49773 | | 12/1998 |
| WO | WO 99/39298 | | 8/1999 |
| WO | WO 00/33074 | | 6/2000 |
| WO | WO 01/75438 | | 10/2001 |

OTHER PUBLICATIONS

Microline Solution, LPKF Laser & Electronics AG; LPKF; Art.-Nr. 107658-1 (Jan. 2000) (4pp.).

Terder, L. et al., Electrochemical Patterning of Self-Assembled Monolayers onto Microscopic Arrays of Gold Electrodes Fabricated by Laser Ablation, *Langmuir*, 1996, 12, 5515-5518.

Tahhan, Isam, "Biocompatible Microstructuring of Polymers and Electrodes with an Excimer Laser", MEDICS Workshop 2000 Speakers Abstracts, 2 pp.

Sheppard, Jr. et al. "Electrical Conductivity Measurements Using Microfabricated Interdigitated Electrodes", *Anal. Chem.*, 1993, 65, 1199-1202.

Srinivasan R., et al. "Ultraviolet Laser Ablation of Organic Polymers", *Chem. Rev.*, 1989, 89, 1303-1316.

Zongyi, Q., et al. "Excimer Laser Patterning on Thin Polymer Surfaces for Electrochemical Gas Sensors", Polymer Physics Laboratory, Changchun Institute of Applied Chemistry, Chinese Academy of Sciences, Changchun, Peop. Rep. China., Proceedings of the International Conference on Lasers (1999) 21st (Abstract) 1pp.

Vaucher et al. "Laser Direct Imaging and Structuring: An Update", http://www.circuitree.com/CDA/ArticleInformation/features/BNP_Features_Item/0,2133,81173.00.html; posted on: Aug. 1, 2002.

Wu, J. et al. "Single-shot Excimer Laser Ablation of Thick Polymer Resists on Metallic Substrates", AMP Journal of Technology vol. 1, Nov. 1991, 69-79.

Srinivasan, R., "Ablation of Polymers and Bilogical Tisssue by Ultraviolet Lasers", Science, vol. 234, Oct. 21, 1986, 559-564.

Colon, W., "Microanalysis: Biosensors at the Point of Care", MST News 01/04, pp. 9-11.

Duley, W.W. "UV Lasers: effects and applications in materials science", Chapter 3 Photochemical and photothermal effects, Cambridge University Press, pp. 78-97.

* cited by examiner

METHOD OF MAKING A BIOSENSOR

CROSS REFERENCE TO RELATED APPLICATIONS

This application is a divisional of U.S. application Ser. No. 09/942,515, filed 29 Aug. 2001, now U.S. Pat. No. 6,814,844.

FIELD OF THE INVENTION

The present invention relates to a biosensor, more particularly to an electrochemical biosensor with a code pattern thereon.

BACKGROUND AND SUMMARY OF THE INVENTION

Electrochemical biosensors are known. They have been used to determine the concentration of various analytes from biological samples, particularly from blood. Electrochemical biosensors are described in U.S. Pat. Nos. 5,413,690; 5,762,770; 5,798,031; and 5,997,817 the disclosure of each of which is expressly incorporated herein by reference. It is also known to include a code on a test strip that identifies the manufacturing batch of the strip. See WO 99/22236.

According to one aspect of the present invention a biosensor is provided. The biosensor comprises a support substrate, an electrically conductive coating positioned on the support substrate, the coating being formed to define electrodes and a code pattern, wherein there is sufficient contrast between the conductive coating and the substrate such that the code pattern is discernible, and at least one reagent positioned on at least one electrode.

According to another aspect of the present invention a biosensor is provided. The biosensor comprises a support substrate, an electrically conductive coating positioned on the support substrate, the coating being formed to define electrodes and a code pattern, wherein there is sufficient contrast between the conductive coating and the substrate such that the code pattern is discernible, and a cover cooperating with the support substrate to define a channel. At least a portion of the electrodes are positioned in the channel.

In addition, a method of forming a biosensor is provided in accordance with the present invention. The method comprises the steps of providing a substrate coated with a electrically conductive material, ablating the electrically conductive material to form electrodes and a code pattern, wherein there is sufficient contrast between the conductive coating and the substrate such that the code pattern is discernible, and applying a reagent to at least one of the electrodes.

Still further, in accordance with the present invention a biosensor is provided. The biosensor comprises a support substrate and an electrically conductive coating positioned on the support substrate. The coating is formed to define electrodes and means for identifying the biosensor, wherein there is sufficient contrast between the conductive coating and the substrate such that the identifying means is discernible.

Additional features of the invention will become apparent to those skilled in the art upon consideration of the following detailed description of the preferred embodiment exemplifying the best mode of carrying out the invention as presently perceived.

BRIEF DESCRIPTION OF THE DRAWINGS

The detailed description particularly refers to the accompanying figures in which.

DETAILED DESCRIPTION OF THE INVENTION

Figure 1:
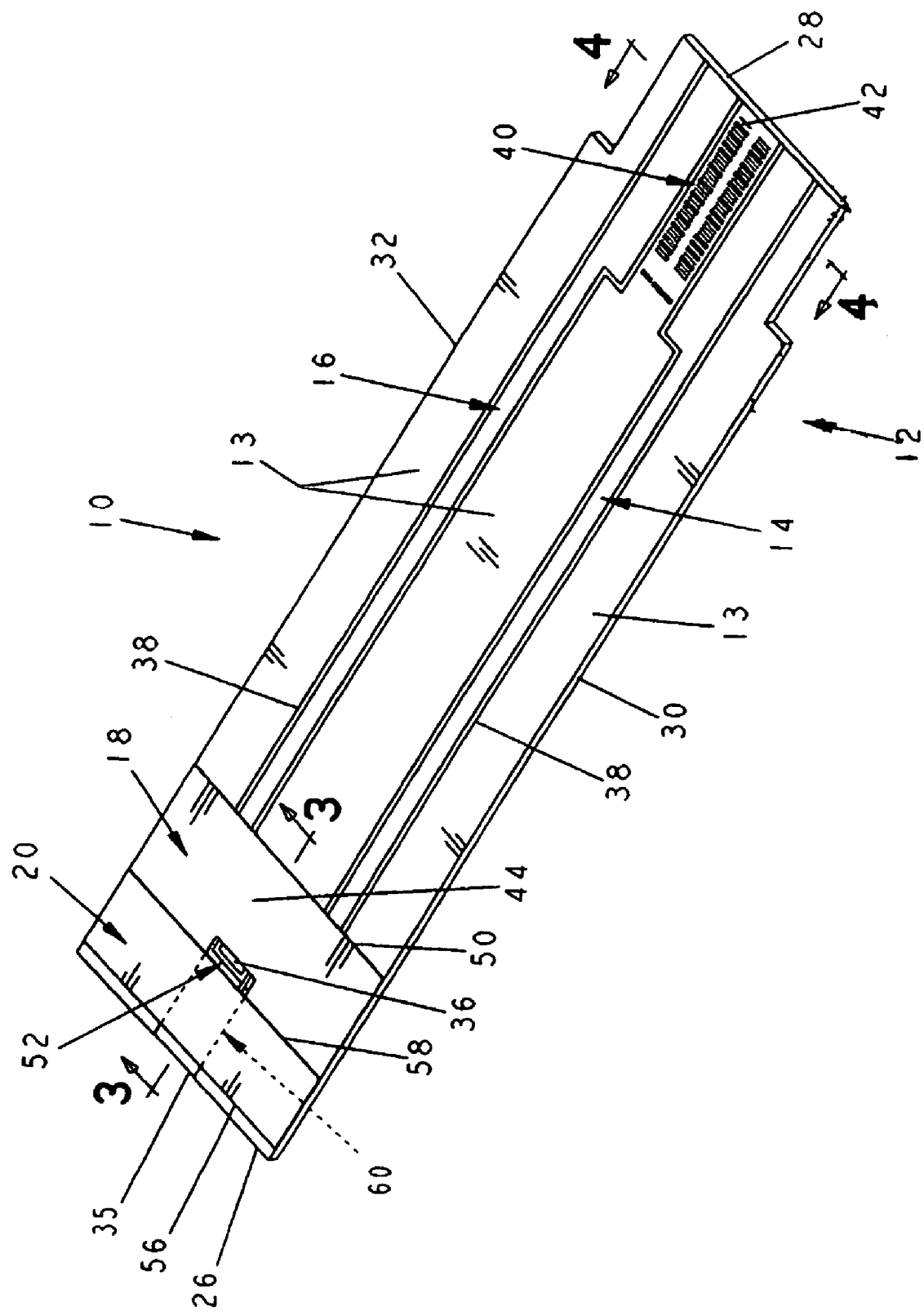
FIG. 1 is a perspective view of a biosensor in accordance with the present invention, showing the biosensor formed to include a code pattern formed thereon.

The present invention relates to a biosensor and a method for manufacturing a biosensor that has a specific code pattern. This code pattern is beneficially formed from the same electrically conductive material and in the same manner as the electrodes of the biosensor, which reduces steps in the manufacturing process. Laser ablation is preferably used in forming the code pattern while generating the electrode pattern. The code pattern can be read in a number of ways, non-limiting examples of which include optically or electrically depending on the structures formed onto the biosensor. The structures could show contrast in their optical reflectivity, their electrical conductivity, or their resistance respectively. The structures could also be high reflectivity areas surrounded by low reflectivity areas or vice versa, or areas of high electrical conductivity surrounded by areas of low conductivity. Aspects of the invention are presented in FIGS. 1-6, which are not drawn to scale and wherein like components in the several views are numbered alike.

FIGS. 1-4 illustrate an aspect of the invention in the form of a biosensor 10 having an electrode-support substrate 12, an electrical conductor 13 positioned on the substrate 12 that is disrupted to define electrodes 14, 16, a spacer substrate 18 positioned on substrate 12, and a cover substrate 20 positioned on the spacer substrate 18. Biosensor 10 is preferably rectangular in shape. It is appreciated however, that biosensor 10 can assume any number of shapes in accordance with this disclosure. Biosensor 10 is preferably produced from rolls of material however, it is understood that biosensor 10 can be constructed from individual sheets in accordance with this disclosure. Thus, the selection of materials for the construction of biosensor 10 necessitates the use of materials that are sufficiently flexible for roll processing, but which are still rigid enough to give a useful stiffness to finished biosensor 10.

Figure 2:
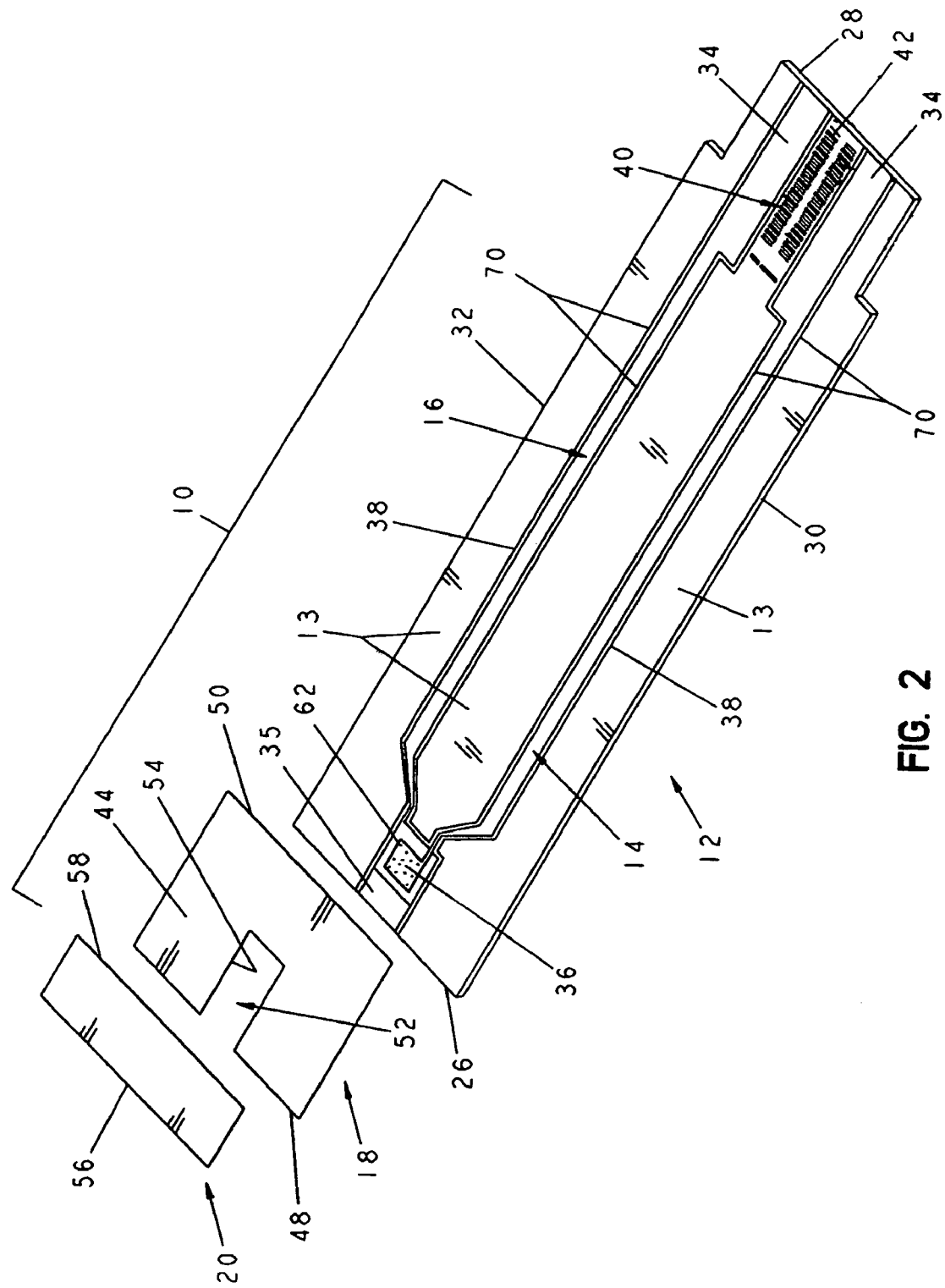
FIG. 2 is an exploded assembly view of the biosensor of FIG. 1, showing the biosensor including an electrode array positioned at one end, a spacer substrate including a notch, and a cover formed to extend over a portion of the notch.
Figure 4:
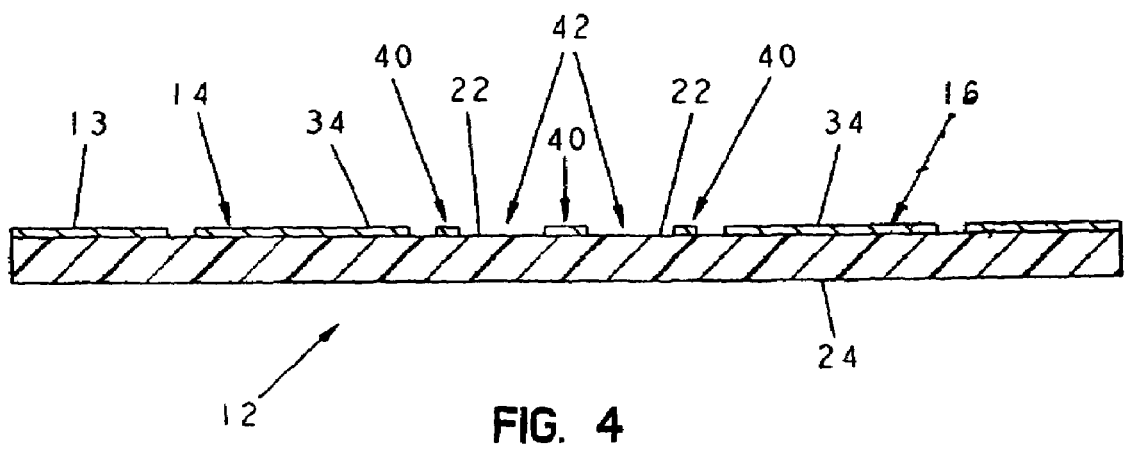
FIG. 4 is a view taken along lines 4-4 of FIG. 1.

Referring to FIG. 4, the support substrate 12 includes a first surface 22 facing the spacer substrate 18 and a second surface 24. In addition, as shown in FIG. 2, substrate 12 has opposite first and second ends 26, 28 and opposite edges 30, 32 extending between the first and second ends 26, 28. Substrate 12 is generally rectangular in shape, it is appreciated however, that support may be formed in a variety of shapes and sizes in accordance with this disclosure. Substrate 12 is formed of a flexible polymer and preferably from a flexible polymer and preferably from a polymer such as a polyester or polyimide, polyethylene naphthalate (PEN). A non-limiting example of a suitable PEN is 5 mil (125 um) thick KALADEX®, a PEN film commercially available from E.I. DuPont de Nemours, Wilmington, Del., which is coated with gold by ROWO Coating, Henbolzhelm, Germany.

Electrodes 14, 16 are created or isolated from conductor 13 on first surface 22 of substrate 12. Non-limiting examples of a suitable electrical conductor 13 include aluminum, carbon (such as graphite), cobalt, gallium, gold, indium, iridium, iron, lead, magnesium, mercury (as an amalgam), nickel, niobium, osmium, palladium, platinum, rhenium, rhodium, selenium, silicon (such as highly doped polycrystalline silicon), silver, tantalum, tin, titanium, tungsten, uranium, vanadium, zinc, zirconium, mixtures thereof, and alloys, oxides, or metallic compounds of these elements. Preferably, electrical conductor 13 is selected from the following materials: gold, platinum, palladium, iridium, or alloys of these metals, since such noble metals and their alloys are unreactive in biological systems. Most preferably, electrical conductor 13 is gold.

Electrodes 14, 16 are isolated from the rest of the electrical conductor 13 by laser ablation. See FIG. 4. Techniques for forming electrodes on a surface using laser ablation are known. See, for example, U.S. patent application Ser. No. 09/411,940, filed Oct. 4, 1999, now U.S. Pat. No. 6,662,439 and entitled "LASER DEFINED FEATURES FOR PATTERNED LAMINATES AND ELECTRODE", the disclosure of which is expressly incorporated herein by reference. Preferably, electrodes 14, 16 are created by removing the electrical conductor 13 from an area extending around the electrodes to form a gap of exposed support substrate 12. Therefore, electrodes 14, 16 are isolated from the rest of the electrically-conductive material on substrate 12 by a gap having a width of about 25 μm to about 500 μm, preferably the gap has a width of about 100 μm to about 200 μm. Alternatively, it is appreciated that electrodes 14, 16 may be created by laser ablation alone on substrate 12. It is appreciated that while laser ablation is the preferred method for forming electrodes 14, 16 given its precision and sensitivity, other techniques such as lamination, screen-printing, or photolithography may be used in accordance with this disclosure.

As shown in FIG. 2, electrodes 14, 16 cooperate with one another to define an electrode array 36. In addition, electrodes 14, 16 each include a contact 34 and a lead 38 extending between the contact 34 and the array 36. It is appreciated that the leads 38 extending from the array can be formed to have many lengths and extend to a variety of locations on the electrode-support substrate 12. It is appreciated that the configuration of the electrode array, the number of electrodes, as well as the spacing between the electrodes may vary in accordance with this disclosure and that a greater than one array may be formed as will be appreciated by one of skill in the art.

Referring again to FIGS. 2 and 3, a recess 35 is formed from the electrical conductor 13 by laser ablation using techniques as described above. Recess is created by removing the electrical conductor 13 to expose the first surface 22 of the support substrate 12 adjacent to the first end 26. It is appreciated that a portion of the first surface 22 may also be removed to form the recess 35 in accordance with this disclosure.

Figure 5:
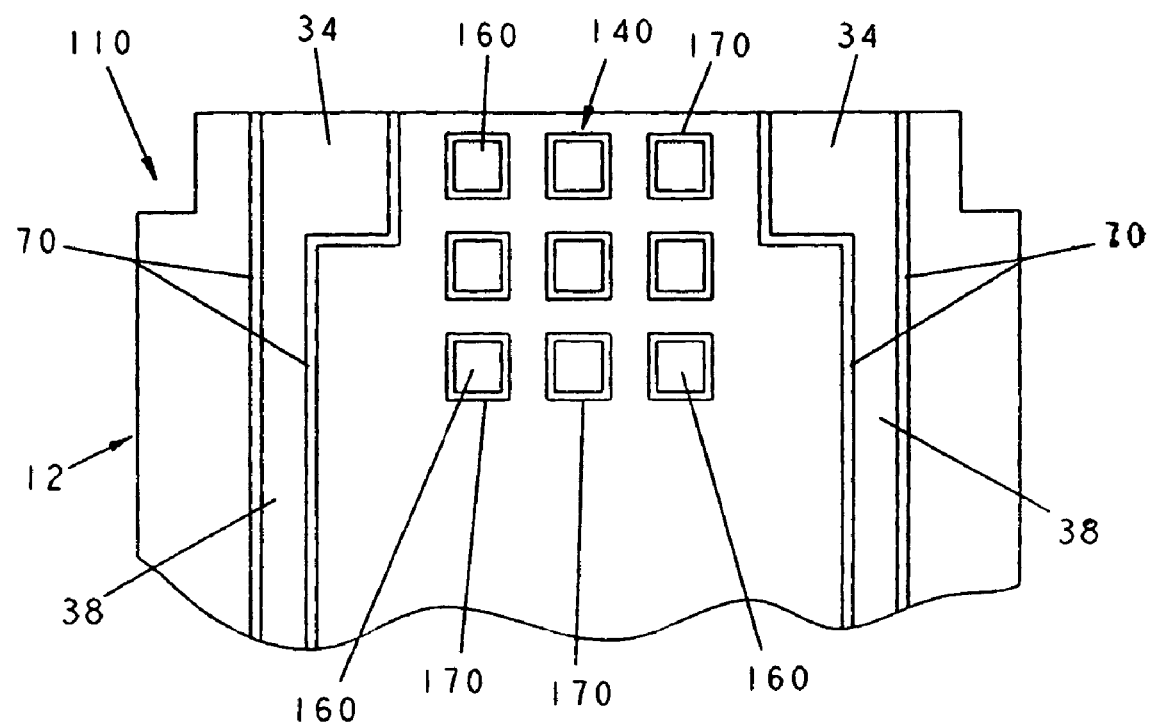
FIG. 5 is an enlarged top view of an alternative code pattern formed on a biosensor in accordance with the present invention.
Figure 6:
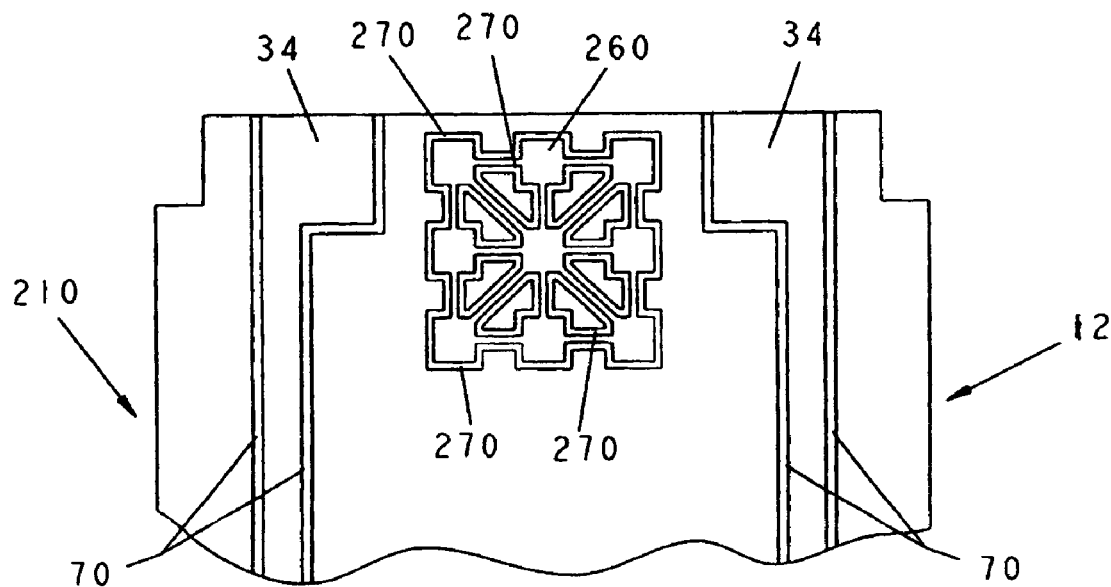
FIG. 6 is an enlarged top view of an alternative code pattern formed on a biosensor in accordance with the present invention.

In addition, as shown in FIGS. 1, 2, and 4, the discernible code pattern 40 is formed from the electrical conductor 13 by laser ablation using techniques as described above with reference to electrodes 14, 16. Specifically, the code pattern 40 is created by removing the electrical conductor 13 in a pre-defined pattern to expose the first surface 22 of the support substrate 12. While pattern 40 is illustratively a barcode type pattern, it is appreciated that the pattern 40 can take on any number of shapes and patterns, non-limiting examples of which are shown in FIGS. 5 and 6.

It is also appreciated that the pattern 40 can be provided in a human readable, optical readable, or electrical readable form in accordance with this disclosure. The structures could show contrast in their optical reflectivity, their electrical conductivity, or their resistivity respectively. To aid in contrasting the electrical conductivity of the code pattern 40, the electrical conductor 13 of the pattern 40 may be coated with a second conductive material (not shown) that is different from the electrical conductor 13. Non-limiting examples of the second conductive material include carbon and silver. It is appreciated, however, that a wide variety of materials may be coated on the electrical conductor 13 to change the electrical property of the code pattern 40.

It is also appreciated; electrodes 14, 16 could be formed from layers of electrically conductive materials having different colors, reflectivity, conductance, etc. Thus, the code pattern can be formed by removing a portion of the electrical conductor layers, leaving behind areas of high reflectivity surrounded by low reflectivity areas or vice versa, areas of high electrical conductivity surrounded by areas of low conductivity or vise versa. It is also possible to laser etch a code pattern that has a known resistance and this area can be read electrochemically to identify or recognize the code pattern. Moreover, it is appreciated that the code pattern can be a combination of any of the above readable forms in accordance with the present invention.

As shown in FIG. 4, the code pattern 40 is isolated from the rest of the electrically conductive material 13 on substrate 12 by gaps 42. Gaps 42 can have a wide variety of widths in accordance with this disclosure depending upon the specific use of the code pattern 40. Non-limiting examples of widths of the gaps include from about 1 μm to about 1000 μm. Alternatively, it is appreciated that the code pattern 40 may be created by laser ablation alone on substrate 12. It is appreciated that while laser ablation is the preferred method for forming the code pattern 40 given its precision and sensitivity, other techniques such as lamination, screen-printing, or photolithography may be used in accordance with this disclosure.

The manufacturer of biosensor 10 may maintain a central database containing a set of code patterns, each of which uniquely identifies an individual biosensor, or batch of biosensors. There may also be associated with each code pattern a set of calibration data for the biosensor 10. It is appreciated that the code patterns may be associated with any number of identification or data sets in accordance with the present invention.

Spacer substrate 18 of biosensor 10 includes an upper surface 44 and a lower surface 46 facing the substrate 12. In addition, the spacer substrate 18 includes opposite first and second ends 48, 50. First end 48 includes a notch 52, which is defined by a border 54. The border illustratively includes three generally linear sides. It is appreciated that the notch can take on a variety of shapes and sizes in accordance with this disclosure. When biosensor 10 is assembled, the border 54 extends about at least a portion of the array 36 so that the array 36 is at least partially exposed in the notch 52.

Spacer substrate 18 is formed of a flexible polymer and preferably from a flexible polymer and preferably from a polymer such as an adhesive coated polyethylene terephthalate (PET) polyester. A non-limiting example of a suitable PET is 3 mil (75 um) thick white PET film both sides of which are coated with a pressure-sensitive adhesive (Product #ARcare 8877) commercially available from Adhesives Research, Inc. Glen Rock, Pa. It is appreciated that spacer substrate 18 may be constructed of a variety of materials and may be coupled to the substrate 12 and the cover substrate 20 using a wide variety of commercially available adhesives, or by welding (heat or ultrasonic) when large portions of the surface 22 of the electrode support substrate 12 are exposed and not covered by electrical conductor 13.

The cover substrate 20 is coupled to the upper surface 44 of the spacer substrate 18. See FIG. 3. The cover substrate 20 includes opposite first and second ends 56, 58. The cover substrate 20 is coupled to the spacer substrate 18 such that the first end 56 is spaced-apart from the end 48 of the spacer substrate 18 and the second end 58 is spaced-apart from the end 50 of the spacer substrate 18. When biosensor 10 is assembled, cover substrate 20 cooperates with the spacer support 20 and the electrode-support 12 to define a capillary channel 60.

Cover substrate 20 is generally rectangular in shape, it is appreciated, however, that the cover substrate may be formed in a variety of shapes and sizes in accordance with this disclosure. Cover substrate 20 is formed from a flexible polymer and preferably from a polymer such as polyester. A non-limiting example of a suitable polymer is 3.9 mil (99 um) thick 3M hydrophilic polyester film (3M Product #9971), commercially available from 3M Healthcare, St. Paul, Minn.

Figure 3:
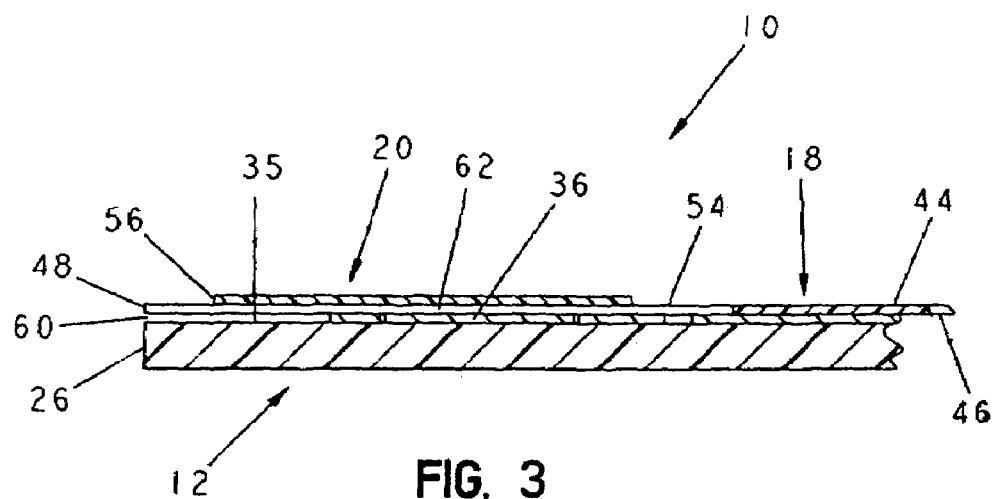
FIG. 3 is a view taken along lines 3-3 of FIG. 1.

Referring now to FIGS. 1 and 3, the capillary channel 60 is generally linear in shape and is defined by the cover substrate 20, the electrode support substrate 12, and the border 54 of the spacer substrate 18. When biosensor 10 is assembled, channel 60 extends across the electrode array 36. Cover substrate 20 does not extend across the entire notch 52, therefore, a portion of the notch serves as an air outlet in accordance with this disclosure.

An electrochemical reagent 62 is positioned on the array 36. The reagent 62 provides electrochemical probes for specific analytes. The term analyte, as used herein, refers to the molecule or compound to be quantitatively determined. Non-limiting examples of analytes include carbohydrates, proteins, such as hormones and other secreted proteins, enzymes, and cell surface proteins; glycoproteins; peptides; small molecules; polysaccharides; antibodies (including monoclonal or polyclonal Ab); nucleic acids; drugs; toxins; viruses of virus particles; portions of a cell wall; and other compounds processing epitopes. The analyte of interest is preferably glucose.

The choice of the specific reagent 62 depends on the specific analyte or analytes to be measured, and are well known to those of ordinary skill in the art. An example of a reagent that may be used in biosensor 10 of the present invention is a reagent for measuring glucose from a whole blood sample. A non-limiting example of a reagent for measurement of glucose in a human blood sample contains 62.2 mg polyethylene oxide (mean molecular weight of 100-900 kilo Daltons), 3.3 mg NATROSOL 244M, 41.5 mg AVICEL RC-591 F, 89.4 mg monobasic potassium phosphate, 157.9 mg dibasic potassium phosphate, 437.3 mg potassium ferricyanide, 46.0 mg sodium succinate, 148.0 mg trehalose, 2.6 mg TRITON X-100 surfactant, and 2,000 to 9,000 units of enzyme activity per gram of reagent. The enzyme is prepared as an enzyme solution from 12.5 mg coenzyme PQQ and 1.21 million units of the apoenzyme of quinoprotein glucose dehydrogenase. This reagent is further described in U.S. Pat. No. 5,997,817, the disclosure of which is expressly incorporated herein by reference.

Non-limiting examples of enzymes and mediators that may be used in measuring particular analytes in biosensor 10 are listed below in Table 1.

TABLE 1

| Analyte | Enzymes | Mediator (Oxidized Form) | Additional Mediator |
|---|---|---|---|
| Glucose | Glucose Dehydrogenase and Diaphorase | Ferricyanide | |
| Glucose | Glucose-Dehydrogenase (Quinoprotein) | Ferricyanide | |
| Cholesterol | Cholesterol Esterase and Cholesterol Oxidase | Ferricyanide | 2,6-Dimethyl-1,4-Benzoquinone 2,5-Dichloro-1,4-Benzoquinone or Phenazine Ethosulfate |
| HDL Cholesterol | Cholesterol Esterase and Cholesterol Oxidase | Ferricyanide | 2,6-Dimethyl-1,4-Benzoquinone 2,5-Dichloro-1,4-Benzoquinone or Phenazine Ethosulfate |
| Triglycerides | Lipoprotein Lipase, Glycerol Kinase, and Glycerol-3-Phosphate Oxidase | Ferricyanide or Phenazine Ethosulfate | Phenazine Methosulfate |
| Lactate | Lactate Oxidase | Ferricyanide | 2,6-Dichloro-1,4-Benzoquinone |
| Lactate | Lactate Dehydrogenase and Diaphorase | Ferricyanide Phenazine Ethosulfate, or Phenazine Methosulfate | |
| Lactate Dehydrogenase | Diaphorase | Ferricyanide | Phenazine Ethosulfate, or Phenazine Methosulfate |
| Pyruvate | Pyruvate Oxidase | Ferricyanide | |
| Alcohol | Alcohol Oxidase | Phenylenediamine 1-Methoxy-Phenazine Methosulfate | |
| Bilirubin | Bilirubin Oxidase | | |
| Uric Acid | Uricase | Ferricyanide | |

In some of the examples shown in Table 1, at least one additional enzyme is used as a reaction catalyst. Also, some of the examples shown in Table 1 may utilize an additional mediator, which facilitates electron transfer to the oxidized form of the mediator. The additional mediator may be provided to the reagent in lesser amount than the oxidized form of the mediator. While the above assays are described, it is contemplated that current, charge, impedance, conductance, potential, or other electrochemically indicated property of the sample might be accurately correlated to the concentration of the analyte in the sample with biosensor 10 in accordance with this disclosure.

A plurality of biosensors 10 are typically packaged in a vial, usually with a stopper formed to seal the vial. It is appreciated, however, that biosensors 10 may be packaged individually, or biosensors can be folded upon one another, rolled in a coil, stacked in a cassette magazine, or packed in blister packaging.

Biosensor 10 is used in conjunction with the following:

1. a power source in electrical connection with contacts 34 and capable of supplying an electrical potential difference between electrodes 14, 16 sufficient to cause diffusion limited electro-oxidation of the reduced form of the mediator at the surface of the working electrode; and 2. a meter in electrical connection with contacts 34 and capable of measuring the diffusion limited current produced by oxidation of the reduced form of the mediator with the above-stated electrical potential difference is applied.

The meter is provided with a pattern reader that is capable of reading the code pattern 40 into a memory of the meter. The reader can be an electrical or optical reader in accordance with the present invention. The reader is formed to read the code pattern 40 when the bisoensor 10 is inserted into the meter. When, however, the code pattern is in a human readable form, it is appreciated that the meter may include an interface, which permits the user to input the information from the code pattern manually. There are many ways to optically read code pattern 40 such as laser scanners, pen-like wands, and charge-couple-device (CCD) scanners. A non-limiting example of a suitable optical reader suitable for use with the present invention includes a light emitting diode(s) (LED), a lens, and a photodiode. It is appreciated that the reader may be an independent internal component of the meter.

The meter may further be formed to transfer the code pattern from the meter to a memory unit where it is stored. It is appreciated that the memory unit can be formed to store information regarding the specifics of the code pattern as well as patient information including previous meter readings. The meter will normally be adapted to apply an algorithm to the current measurement, whereby an analyte concentration is provided and visually displayed. Improvements in such power source, meter, and biosensor system are the subject of commonly assigned U.S. Pat. No. 4,963,814, issued Oct. 16, 1990; U.S. Pat. No. 4,999,632, issued Mar. 12, 1991; U.S. Pat. No. 4,999,582, issued Mar. 12, 1991; U.S. Pat. No. 5,243,516, issued Sep. 7, 1993; U.S. Pat. No. 5,352,351, issued Oct. 4, 1994; U.S. Pat. No. 5,366,609, issued Nov. 22, 1994; White et al., U.S. Pat. No. 5,405,511, issued Apr. 11, 1995; and White et al., U.S. Pat. No. 5,438,271, issued Aug. 1, 1995, the disclosures of each of which are expressly hereby incorporated by reference.

Many fluid samples may be analyzed. For example, human body fluids such as whole blood, plasma, sera, lymph, bile, urine, semen, cerebrospinal fluid, spinal fluid, lacrimal fluid and stool specimens as well as other biological fluids readily apparent to one skilled in the art may be measured. Fluid preparations of tissues can also be assayed, along with foods, fermentation products and environmental substances, which potentially contain environmental contaminants. Preferably, whole blood is assayed with this invention.

To manufacture biosensor 10 a roll of metallized electrode support material is fed through guide rolls into an ablation/washing and drying station. A laser system capable of ablating support 12 is known to those of ordinary skill in the art. Non-limiting examples of which include excimer lasers, with the pattern of ablation controlled by mirrors, lenses, and masks. A non-limiting example of such a custom fit system is the LPX-300 or LPX-200 both commercially available from LPKF Laser Electronic GmbH, of Garbsen, Germany.

In the laser ablation station, the metallic layer of the metallized film is ablated in a pre-determined pattern, to form a ribbon of isolated electrode sets on the electrode support material, code patterns, and a recess in the film adjacent to each electrode array. To ablate electrodes 14, 16, recess 35, and code patterns 40 in 50 nm thick gold conductor 13, 90 mJ/cm$^2$ energy is applied. It is appreciated, however, that the amount of energy required may vary from material to material, metal to metal, or thickness to thickness. The ribbon is then passed through more guide rolls, with a tension loop and through an optional inspection system where both optical and electrical inspection can be made. The system is used for quality control in order to check for defects.

Upon leaving the laser ablation station, the metallized film is fed into a reagent dispensing station. Reagents that have been compounded are fed into a dispensing station where it is applied in a liquid form to the center of respective the array 34. Reagent application techniques are well known to one of ordinary skill in the art as described in U.S. Pat. No. 5,762,770, the disclosure of which is expressly incorporated herein by reference. It is appreciated that reagents may be applied to the array 34 in a liquid or other form and dried or semi-dried onto the array 34 in accordance with this disclosure.

In a separate process, a double-sided pressure-sensitive film with dual release liners is fed into a window punch unit where notches are formed. The film is then fed into a lamination & kiss-cutting station. At the same time, a roll of cover substrate material is fed over a guide roll into the lamination & kiss-cutting station, where the release liner is removed from the upper surface 44 and rewound into a roll. The upper surface 33 of the spacer substrate material is applied to the cover substrate material. Next, the film is kiss cut and a portion of the cover substrate material is removed, leaving behind the cover substrate material coupled to the spacer substrate material, extending across a portion of the notch.

The cover material/spacer substrate subassembly is fed into a sensor lamination & cut/pack station. The reagent-coated electrode-support substrate material is fed from the dispensing station into the sensor lamination & cut/pack station as well. The remaining release liner is removed from the spacer substrate and the spacer substrate is positioned on the electrode-support substrate material so that at least a portion of the electrode array 36 is aligned with the notch 52. Next, the resulting assembled material is cut to form individual biosensors 10, which are sorted and packed into vials, each closed with a stopper, to give packaged biosensor strips.

In use, the meter is turned on and the biosensor is inserted into the meter. It is appreciated that the user may turn on the meter, or it may turn on automatically upon insertion of the biosensor. The LED emits a light that is directed through a lens towards the code pattern of the biosensor. The light is reflected off of the code pattern, through the lens, and toward the photodiode. The photodiode measures the intensity of the light that is reflected back from the code pattern and generates a corresponding voltage waveform. A decoder deciphers this waveform and translates it into a reading of the code pattern. It is appreciated that many commercially available optical readers may be used in accordance with the present invention. Preferably, the optical reader will be custom fit reader.

In use, a user of biosensor 10 places a finger having a blood collection incision against the recess 35 in the notch 52. Capillary forces pull a liquid blood sample flowing from the incision through the capillary channel 60 across the reagent 62 and the array 34. The liquid blood sample dissolves the reagent 62 and engages the array 34 where the electrochemical reaction takes place.

In use for example, after the reaction is complete, a power source (e.g., a battery) applies a potential difference between the electrodes 14, 16 respectively. When the potential difference is applied, the amount of oxidized form of the mediator at the reference electrode and the potential difference must be sufficient to cause diffusion-limited electro-oxidation of the reduced form of the mediator at the surface of the working electrode. A current measuring meter (not shown) measures the diffusion-limited current generated by the oxidation of the reduced form of the mediator at the surface of the working electrode.

The measured current may be accurately correlated to the concentration of the analyte in sample when the following requirements are satisfied:

1. The rate of oxidation of the reduced form of the mediator is governed by the rate of diffusion of the reduced form of the mediator to the surface of the working electrode.

2. The current produced is limited by the oxidation of reduced form of the mediator at the surface of the working electrode.

The processes and products described above include disposable biosensor 10 especially for use in diagnostic devices. Also included, however, are electrochemical sensors for non-diagnostic uses, such as measuring an analyte in any biological, environmental, or other sample. As discussed above, biosensor 10 can be manufactured in a variety of shapes and sizes and be used to perform a variety of assays, non-limiting examples of which include current, charge, impedance conductance, potential or other electrochemical indicative property of the sample applied to biosensor.

In accordance with another embodiment of the present invention, biosensor 110 is illustrated in FIG. 5. Biosensor 110 is formed in a similar manner to biosensor 10 except that biosensor 110 includes a code pattern 140. Code pattern 140 includes nine isolated pads 160. It is appreciated that the number of pads can be greater or fewer than nine in accordance with this disclosure. Each pad 160 is separated by from the surrounding electrical conductor by a gap 170.

Code pattern 140 is used once biosensor 110 is attached to a meter circuit board (not shown) that includes a connector. Generally, the connector will include two contacts per possible pad location on biosensor 110. Code pattern 140 of the present invention enables the meter to check continuity at each pad 160 location or determine that a pad does not exist in a pre-determined location. If a pad 160 is present, the meter will recognize the presence of a pad 160 by a continuity check. One of ordinary skill in the art will be well aware of methods suitable for performing a continuity check.

Code pattern 140 is formed from the electrical conductor by laser ablation using techniques as described above with reference to electrodes 14, 16, shown for example in FIG. 1. Specifically, removing the electrical conductor in a pre-defined pattern to expose the first surface of the support substrate 12 creates the code pattern 140. Code pattern 140 can also be coated with a second electrical conductor (not shown) to modify the electrical resistivity of the pattern 140. While pattern 140 illustratively includes nine spaced-apart generally square-shaped pads, it is appreciated that the pattern 140 can take on any number of shapes and patterns in accordance with this disclosure. In addition, it is appreciated that the pattern 140 can be read optically or electrically in accordance with this disclosure.

In use, when the user inserts biosensor 110 into the meter (not shown), the biosensor 110 makes contact to the connector and the electronics of the meter inquire as to how many pads 160 are showing continuity. Predetermined lot information may be stored in a memory unit of the meter. It is appreciated that the memory unit may also store a variety of patient information including previous meter readings. This memory unit is formed with memory components, a non-limiting example of which is known as RAM, which is well known in the prior art. The results of the continuity query may be used to set the appropriate code information in the meter, which enables the meter to eliminate chemistry or reagent variation.

In accordance with another embodiment of the present invention, biosensor 210 is illustrated in FIG. 6. Biosensor 210 is formed in a similar manner to biosensor 10, except that biosensor 210 includes a code pattern 240. Code pattern 240 includes nine pads 260 that are in communication with one another. It is appreciated that the number of pads can vary in accordance with this disclosure. Each pad 260 is separated from the surrounding electrical conductor by gaps 270.

Code pattern 240 is formed from the electrical conductor by laser ablation using techniques as described above with reference to electrodes 14, 16, shown for example in FIG. 1. Specifically, removing the electrical conductor in a pre-defined pattern to expose the first surface of the support substrate 12 creates the code pattern 240. Code pattern 240 can also be coated with a second electrical conductor (not shown) to modify the electrical resistivity of the pattern 240.

While pattern 240 illustratively includes nine generally square-shaped pads that are interconnected, it is appreciated that the pattern 240 can take on any number of shapes and patterns in accordance with this disclosure, which would give various resistance levels. These differing resistance levels can be correlated to a reagent lot. For example, the pattern 240 can be varied by disconnecting the internal links between the pads 260. This disconnection can be done, for example, by a laser. By changing the number of interconnected pads, the resistance of the remaining interconnected pads 260 will be different. In addition, it is appreciated that the pattern 240 can be read optically or electrically in accordance with this disclosure.

In use, when the user inserts biosensor 210 into the meter (not shown), the biosensor 210 makes contact to the connector and the electronics of the meter inquire as to how many pads 260 are showing continuity. Information related to this continuity is similar to that previously described with reference to biosensor 110.

In addition, the biosensor 210 will make contact with electronics of the meter, which determines the resistance between the interconnected pads. Thus, in preferred embodiments, the meter will determine which pads exist on the biosensor 210, and the resistance of the interconnected pads 260. The information can be stored in the meter as described above with reference to biosensors 10 and 110.

Although the invention has been described in detail with reference to a preferred embodiment, variations and modifications exist within the scope and spirit of the invention, on as described and defined in the following claims.

What is claimed is:

1. A method of forming a biosensor, the method comprising the steps of:
   providing a flexible substrate coated with an electrically conductive material,
   ablating through the electrically conductive material to expose the substrate in a pre-defined pattern so as to form a pattern of electrodes and a code pattern electrically isolated from the electrodes, wherein there is sufficient contrast between the conductive material and the exposed substrate such that the code pattern is discernible, and
   applying a reagent to at least one of the electrodes.

2. The method of claim 1 wherein the ablating step includes the step of laser ablating the electrically conductive material.

3. The method of claim 1 wherein the ablating step includes forming a bar code shaped code pattern.

4. The method of claim 1 wherein the ablating step includes forming a code pattern that includes pads isolated from the surrounding electrically conductive material.

* * * * *